(12) United States Patent
Ratering (10) Patent No.: US 10,241,087 B2
(45) Date of Patent: Mar. 26, 2019

(54) DEVICE FOR THE NON-DESTRUCTIVE ULTRASOUND TESTING OF WORKPIECES WITH IMPROVED HANDLING AND METHOD

(71) Applicant: GE Sensing & Inspection Technologies GmbH, Hürth (DE)

(72) Inventor: Ralf Ratering, Hürth (DE)

(73) Assignee: GE Sensing & Inspection Technologies GmbH, Hurth (DE)

( * ) Notice: Subject to any disclaimer, the term of this patent is extended or adjusted under 35 U.S.C. 154(b) by 3 days.

(21) Appl. No.: 15/127,038

(22) PCT Filed: Mar. 18, 2015

(86) PCT No.: PCT/EP2015/055609
§ 371 (c)(1),
(2) Date: Sep. 19, 2016

(87) PCT Pub. No.: WO2015/140192
PCT Pub. Date: Sep. 24, 2015

(65) Prior Publication Data
US 2017/0115254 A1 Apr. 27, 2017

(30) Foreign Application Priority Data

Mar. 21, 2014 (DE) .................. 10 2014 103 945

(51) Int. Cl.
*G01N 29/26* (2006.01)
*G01N 29/22* (2006.01)

(52) U.S. Cl.
CPC .......... *G01N 29/226* (2013.01); *G01N 29/22* (2013.01); *G01N 29/262* (2013.01); *G01N 2291/0289* (2013.01)

(58) Field of Classification Search
CPC .............. G01N 29/226; G01N 29/262; G01N 2291/0289
(Continued)

(56) References Cited

U.S. PATENT DOCUMENTS 5,161,413 A * 11/1992 Junker ................ G01N 29/223
73/634
5,476,010 A * 12/1995 Fleming ............. G01N 29/0609
340/980

(Continued)

FOREIGN PATENT DOCUMENTS

DE     102004044007 A1    5/2005
DE    1002007015746 A1   10/2008
(Continued)

OTHER PUBLICATIONS

International Search Report and Written Opinion issued in connection with corresponding PCT application PCT/EP2015/055609 dated Jun. 23, 2015.
(Continued)

*Primary Examiner* — Jacques M Saint Surin
(74) *Attorney, Agent, or Firm* — Mintz Levin Cohn Ferris Glovsky and Popeo, P.C.

(57) ABSTRACT

The present embodiments relate to a device for the non-destructive ultrasound testing of workpieces. The device comprises an ultrasonic test probe with an ultrasonic transducer, the ultrasonic test probe being configured for generating and coupling ultrasonic signals into a workpiece or/and for receiving ultrasonic signals from the workpiece. Furthermore, an electronic control unit is provided. The ease of operation is improved as a whole by a special configuration of the test probe and the control unit. Furthermore, the embodiments relate to a method for the non-destructive ultrasound testing of workpieces.

19 Claims, 4 Drawing Sheets

(58) Field of Classification Search
USPC .......................................................... 73/632
See application file for complete search history.

(56) References Cited

U.S. PATENT DOCUMENTS

| | | | |
|---|---|---|---|
| 5,970,438 A * | 10/1999 | Clark ........................ | B61K 9/08 |
| | | | 702/184 |
| 9,675,322 B2 * | 6/2017 | Hoppmann ............... | A61B 8/14 |
| 2005/0131700 A1 | 6/2005 | Washburn et al. | |
| 2006/0225508 A1 * | 10/2006 | Sfeir ........................ | G01B 17/02 |
| | | | 73/602 |
| 2007/0093713 A1 | 4/2007 | Byron | |
| 2007/0225931 A1 | 9/2007 | Morse et al. | |
| 2010/0160786 A1 | 6/2010 | Nordgren | |
| 2010/0212429 A1 * | 8/2010 | Isobe ................... | G01N 29/069 |
| | | | 73/602 |
| 2013/0125657 A1 | 5/2013 | Fonda et al. | |

FOREIGN PATENT DOCUMENTS

| | | | |
|---|---|---|---|
| ES | 2024352 | * | 2/1992 |
| JP | 2733311 B2 | | 3/1998 |

OTHER PUBLICATIONS

Unofficial English Translation of German Search Report issued in connection with corresponding DE Application No. 102014103945.9 dated Nov. 19, 2014.

* cited by examiner

DEVICE FOR THE NON-DESTRUCTIVE ULTRASOUND TESTING OF WORKPIECES WITH IMPROVED HANDLING AND METHOD

BACKGROUND

Embodiments relate to a device for the non-destructive ultrasound testing of workpieces, in particular an ultrasonic test probe on which an input unit is disposed that is configured for transmitting control commands from a user to an electronic control unit.

The use of pulsed ultrasonic signals for the non-destructive testing of workpieces has been known for years from a variety of methods in material testing. Generally, an ultrasonic test probe is coupled to the test piece using a couplant, generally water or gel. The ultrasonic test probe comprises an ultrasonic transducer that is suitable for generating ultrasonic signals and transmit them into the workpiece to be tested. They are at least partially reflected both on the boundary surfaces of the workpiece and on internal defects (e.g. cracks, pipes, inhomogeneities in the material, etc.) and can be detected by an ultrasonic transducer working as a receiver. In the pulse-echo method, the ultrasonic transducer is suitable to be used both as a transmitter as well as a receiver. In inspections according to the transsonification principle, a second ultrasonic transducer serves as a receiver disposed on the workpiece to be tested at a distance from the first ultrasonic transducer. The ultrasonic test probe is selected depending on the geometry, the other properties of the workpiece to be inspected and the testing task.

The inspected testing region can be changed both by mechanical movement and the arrangement of ultrasonic test probes as well as by changing the ultrasound parameters of the ultrasonic signals coupled into the workpiece, if phased-array test probes with phase-accurately controllable transducer segments are used.

The receiver converts the received ultrasonic signals into electrical signals. The electrical signals are then processed, for example amplified or/and filtered, and can be displayed by means of an imaging unit. The sound propagation of the coupled-in ultrasonic signals in the workpiece depends on the material and the ultrasound parameters, such as transmission/reception aperture, insonification angle and focusing depth of the transmitted ultrasonic signals in the workpiece. Depending on what the ultrasonic signals are reflected by, for example by a boundary surface of the workpiece or a flaw within the workpiece (pipe, inhomogeneity in the material, crack), the received ultrasonic signals differ from each other. The position of a flaw can be determined from the transit-time difference between the transmission of the ultrasonic signals and the reception of the reflected ultrasonic signals. The amplitude of the received ultrasonic signals permits drawing conclusions as to the size and the type of the detected flaw. Furthermore, the received ultrasonic signals depend heavily on the orientation and the distance of the flaw relative to the ultrasonic test probe.

In order to be able to give as comprehensive an evaluation as possible of the workpiece to be tested, it may be beneficial if it is possible to process the received ultrasonic signals, for example by the possibility of changing their graphical representation or by amplifying or filtering the received ultrasonic signals. Furthermore, it may be beneficial to perform several inspections with different ultrasound parameters. In most cases, reacting to deviating geometries or other difficulties on-site is troublesome and time-consuming. Possibly, the different ultrasonic test probes have to be attached to the workpiece in order to obtain an optimum result.

DE 102007015746 A1 discloses a device for the non-destructive ultrasound testing with a control unit configured as a "stand-alone" ultrasonic testing device, which is configured for communication with the ultrasonic transducer, is able to graphically display received ultrasonic signals, and has various operating elements. With the operating elements of the ultrasonic testing device, both the ultrasound parameters can be varied and the received ultrasonic signals processed. Depending on the workpiece to be inspected and the local conditions, handling of such a "stand-alone" ultrasonic testing device may be disadvantageous. Usually, it is necessary for the ultrasonic test probe to be guided by a user on the workpiece to be tested. Thus, having to execute inputs on an ultrasonic testing device using the other hand is inconvenient.

Embodiments are based on the object of providing a device and a method for the non-destructive ultrasound testing of workpieces that are easier for a user to handle.

This object is achieved by means of a device and a method as disclosed herein. Other advantages and features are apparent the exemplary embodiments described below, which are to be understood as illustrative, and not as limiting.

BRIEF DESCRIPTION

A device according to the embodiments for the non-destructive ultrasound testing of workpieces comprises an ultrasonic test probe with an ultrasonic transducer. The ultrasonic test probe is configured for generating and coupling ultrasonic signals into a workpiece as well as, optionally, for receiving ultrasonic signals from the workpiece. Within the context of the present application, ultrasonic signals are to be understood to be ultrasonic fields that are emitted in pulsed form. For example, an ultrasonic test probe is used in the pulse-echo method for transmitting/receiving ultrasonic signals, or two ultrasonic test probes are used in the transsonification method, with one of the ultrasonic test probes respectively receiving the emitted signals of the other ultrasonic test probe.

Further, the device according to the embodiments comprises an electronic control unit and an input unit, which is disposed on the ultrasonic test probe and configured for communication with the electronic control unit. The electronic control unit is to be understood as a higher-level control unit that can include the various sub-units, for example for beam control or evaluation. The sub-units that are optionally provided do not necessarily have to be united in a single device.

Within the sense of the application, the term "communication" is to be interpreted broadly. For example, various kinds of data or/and signal transmission, in particular, are included which may take place both via cables as well as wirelessly, for example via WiFi, Bluetooth or infrared or other wireless or cable-based types of transmission. Moreover, communication within the sense of the application is to be considered the wireless or cable-based transmission of binary or analog standard signals and the transmission of digitally encoded data packets via bus systems or digital interfaces.

According to the embodiments, control commands issued by the user by means of the input unit are transmitted to the electronic control unit.

In an embodiment, the input unit comprises at least one mechanical operating element via which the user is able to issue control commands. They are issued, for example, by changing one or more of the following input parameters: actuating force, angle of rotation, deflection angle or contact position, or by a change over time of the aforementioned parameters. In an embodiment, the mechanical operating element has a rest position, relative to which changes of an input parameter are detected. Particularly, the mechanical operating element comprises a key, a switch, a joystick, a rotary knob or a ball. For example, the mechanical operating element comprises a joystick with an operating lever configured in such a way that the operating lever is pivotable in at least one plane. A deflection of the operating lever relative to its rest position can be detected as a change of a deflection angle relative to the rest position and processed by the input unit as a control command by the user.

Moreover, the input unit can be configured in such a way that it detects control commands from a user in the form of voice inputs or by gesture control. For example, the input unit detects control commands from a user in the form of voice inputs. The voice input "Send Pulse" is detected, interpreted and transmitted in the form of a control command to the transmitting/receiving unit by the input unit. Thereupon, the control unit controls the ultrasonic transducer in such a way that the latter emits ultrasonic signals into the workpiece.

In an embodiment, the electronic control unit is configured for generating a snapshot of the received ultrasonic signals in response to a control command from the user. For example, the received ultrasonic signals are graphically displayed by means of an imaging unit, and the control command from the user received via the input unit causes a screenshot of the display or/and the storing of the received ultrasonic signals in a certain file format, such as .txt, .asc or any other suitable format.

In an embodiment, the electronic control unit comprises a transmitting/receiving unit configured for communication with the ultrasonic transducer for the purpose of transmitting or/and receiving ultrasonic signals. Particularly, the transmitting/receiving unit is configured for communication with the input unit.

In an embodiment, the electronic control unit comprises an evaluation unit that is suitable for further processing received ultrasonic signals. For example, these can be displayed in different ways by means of an imaging unit. The evaluation unit is configured for communication with the transmitting/receiving unit.

The ultrasonic test probe comprises a housing in which the ultrasonic transducer is disposed. In a development, the transmitting/receiving unit is also disposed in the housing of the ultrasonic test probe.

In an embodiment, the ultrasonic transducer comprises at least two individually controllable segments that can be controlled in a phase-accurate manner by the transmitting/receiving unit, that is, ultrasonic test probes of the phased-array type are used with preference. In particular, linear arrays of 2D arrays can be used. Thus, different ultrasound parameters can be changed. For example, the transmission or/and reception aperture or/and the insonification angle or/and the transverse angle or/and the focusing depth of the ultrasonic signals in the workpiece or/and the central insonification point of the ultrasonic signals can be specifically influenced. The central insonification point means the point of intersection of the acoustic axis of the ultrasonic field and the workpiece surface. In particular in the case of phased arrays, this can vary depending on the transmission aperture used or the insonification angle without the test probe being moved mechanically.

The term "insonification angle" designates the angle between the surface normal on the workpiece surface in the insonification point and the acoustic axis of the ultrasonic field in the workpiece. The acoustic axis and the surface normal together span the insonification plane E. A gradual change of the insonification angle results in a pivoting of the angle, a so-called "sector scan".

The term "transverse angle" within the context of the present application designates the angle of pivoting of the acoustic axis from the undisturbed insonification plane E, with the insonification angle remaining constant. Such a transverse pivoting is possible, for example, by means of a transmitting test probe having a two-dimensional array of individually controllable transducer segments.

In an embodiment, the change of an ultrasound parameter from a starting parameter towards an end parameter takes place in discrete steps. This is supposed also to include the change of the ultrasound parameter in a single step. The starting parameters of the ultrasonic signal can be predefined by a user prior to a testing sequence. For example, the control commands from a user inputted by means of the input unit state that the insonification angle is to be changed from 20° to 40°. In the case of the discrete change, a first pulse sequence of ultrasonic signals will be transmitted at an insonification angle of 20° (starting parameter) by the ultrasonic transducer into the workpiece, and the next pulse sequence of ultrasonic signals at an insonification angle of 40° (end parameter). In the case of the gradual change, pulse sequences of ultrasonic signals with different insonification angles between 20° and 40° will be transmitted, in each case consecutively, into the workpiece.

In an embodiment, the size or/and the number of steps for changing the ultrasound parameter can be varied via the input unit by means of control commands from a user. Particularly, for changing the size or/and the number of steps for changing an ultrasound parameter, the same control commands apply for all ultrasound parameters, for example the voice commands "up", "down", for increasing/reducing the size or/and number of steps. Furthermore, in a development, the ultrasound parameter whose size or/and number of steps for changing the respective ultrasound parameter is increased or reduced can be selected via another control command, for example by means of a mechanical operating element of the input unit.

In an embodiment, the transmitting/receiving unit is configured for carrying out a "freeze" of the currently set ultrasound parameters in response to a control command from a user received via the input unit. Within the sense of the application, "freeze" means that the currently set ultrasound parameters are stored. In an embodiment, they are then used as new starting parameters for further changes. For example, a "freeze" takes place by actuating a key disposed on the ultrasonic test probe.

In a first embodiment, the electronic control unit comprises a transmitting/receiving unit for the purpose of transmitting or/and receiving ultrasonic signals, and the control commands from a user issued via an input unit are converted by the transmitting/receiving unit for beam control.

In a second embodiment, the electronic control unit comprises a graphical user interface (GUI) with a cursor. The control commands from a user issued by means of the input unit serve for navigating the cursor over a graphical user interface. For example, the cursor is navigated across the graphical user interface by means of a joystick disposed on the ultrasonic test probe, or by voice inputs such as "left, right, . . . ".

In an embodiment, the device is configured in such a way that the two embodiments can exist at the same time, and that it is possible to switch between the two modes for example by means of a switch of the input unit and/or a corresponding operating element in the GUI.

The two embodiments are to be explained below with reference to an exemplary input unit with a mechanical operating element. The control commands from a user are in that case issued, for example, by changing one or more of the following input parameters: actuating force, angle of rotation, deflection angle or contact position. Their change over time may also constitute a control command. However, the person skilled in the art should not have any difficulties in transferring the principle onto differently configured mechanical input units.

According to a first embodiment, the change of an input parameter by a user is converted by the transmitting/receiving unit into a change of ultrasound parameters. In an embodiment, the transmission or/and reception aperture, the insonification angle, the central insonification point or/and the focusing depth of the ultrasonic signals in the workpiece are changed. This list is not to be considered complete.

In an embodiment, only one ultrasound parameter is changed at a time by a user changing an input parameter, with the other ultrasound parameters remaining constant. In particular, the ultrasound parameter that is to be changed can be determined by means of the input unit through an input on the GUI.

For example, the mechanical operating element comprises a joystick with an operating lever configured in such a way that it is pivotable in two planes that are perpendicular to each other. A deflection of the joystick relative to its rest position can be detected as a change of a deflection angle relative to the rest position and as a control command by the user from the input unit. The control command is transmitted to the transmitting/receiving unit of the electronic control unit and used for the control of the ultrasonic test probe.

For example, the change of the deflection angle of the joystick is converted, for example, into a change of the insonification angle of the ultrasonic signal of a phased-array test probe. Pivoting in a plane results in a change of the central angle formed by the ultrasonic field incident upon the workpiece surface with the normal on the workpiece surface. Pivoting the operating lever in another plane changes the transverse angle, with the insonification angle remaining constant.

The change of an input parameter can be converted into a change of an ultrasound parameter by means of a conversion factor, there being respectively associated conversion factors for the various ultrasound parameters and input parameters. In an embodiment, a conversion factor can be respectively increased or reduced by a certain value (+2, +4, + . . . ) or factor (×2, ×4, × . . . ).

For all conversion factors, the same control commands apply for changing them, for example the voice commands "up", "down" for increasing/reducing the conversion factor. Particularly, it is possible to choose via another control command which conversion factor is changed. For example, the variation of the conversion factor takes place via a mechanical operating element of the input unit. For example, the mechanical operating element comprises a key, and the change of the conversion factor takes place by the user actuating the key. In an embodiment, the mechanical operating element comprises two keys, a +key and a −key, wherein an actuation of the +key respectively increases the conversion factor by a certain factor or certain value. In an embodiment, the keys apply for the conversion factors of all ultrasound parameters, and the user is able to choose in a suitable manner which conversion factor is changed. The selection can take place, for example, through a mechanical operating element of the input unit.

According to the second embodiment, a change of an input parameter, for example of a deflection angle, an angle of rotation, an actuating force or a contact position, is used for navigating a cursor over the graphical user interface of the electronic control unit. In an embodiment, the rest position of the mechanical operating element corresponds to the resting position of the cursor within the graphical user interface, and the change of an input parameter results in a movement of the cursor. For example, the movement of an operating element configured as a ball causes a movement of the cursor in two directions in space on the graphical user interface.

In an embodiment, the electronic control unit comprises an evaluation unit. The evaluation unit is configured for communication with the transmitting/receiving unit, and for processing received ultrasonic signals. For example, received ultrasonic signals can be amplified or filtered.

In an embodiment, the graphical user interface is configured to generate different displays of the received ultrasonic signals and to display them on an imaging unit, for example as an A-scan, B-scan or as a sector scan. The effects on the received ultrasonic signal of changing ultrasound parameters can thus be observed in situ.

In an embodiment, the transmitting/receiving unit can be controlled for the purpose of beam control via the graphical user interface of the evaluation unit. Particularly, this is done through buttons on the GUI that can be activated by means of the cursor. Within the sense of the application, the term buttons is to be interpreted broadly and comprises, for example, pull-down menus, entry fields, virtual keys, etc.

In an embodiment, the transmission or/and reception aperture, the insonification angle, the transverse angle, the central insonification point or/and the focusing depth of the ultrasonic signals in the workpiece can be changed via buttons of the graphical user interface. This list is not to be considered complete.

In an embodiment, the graphical user interface moreover has buttons for changing conversion factors or the number or/and size of the steps for changing an ultrasound parameter. For example, the graphical user interface has two entry fields in which a starting parameter and an end parameter for a sector scan can be predefined. This is done, for example, by means of two arrow keys, respectively, next to the entry field, via which the parameter in the corresponding field can be increased or reduced. In another entry field of that type, the number or/and size of the steps can be determined in an equivalent manner, for example. Corresponding entry fields can be provided for other ultrasound parameters.

A method according to embodiments for the non-destructive ultrasound testing of workpieces comprises providing a device comprising an ultrasonic test probe with an ultrasonic transducer, an electronic control unit and an input unit disposed on the ultrasonic test probe. The device can be configured in accordance with one of the embodiments described above. Furthermore, the method comprises the step of actuating the input unit disposed on the ultrasonic test probe for issuing a control command, as well as the step of transmitting the control command to the electronic control unit.

BRIEF DESCRIPTION OF THE DRAWINGS

Exemplary embodiments of devices are described below, supported by the Figures and not to be understood as limiting. Of course, all of the features of the above-described embodiments and the following exemplary embodiments can be combined in any way, provided this is technically possible. Elements that are the same functionally are designated with the same reference numerals. The Figures show.

DETAILED DESCRIPTION

Figure 1:
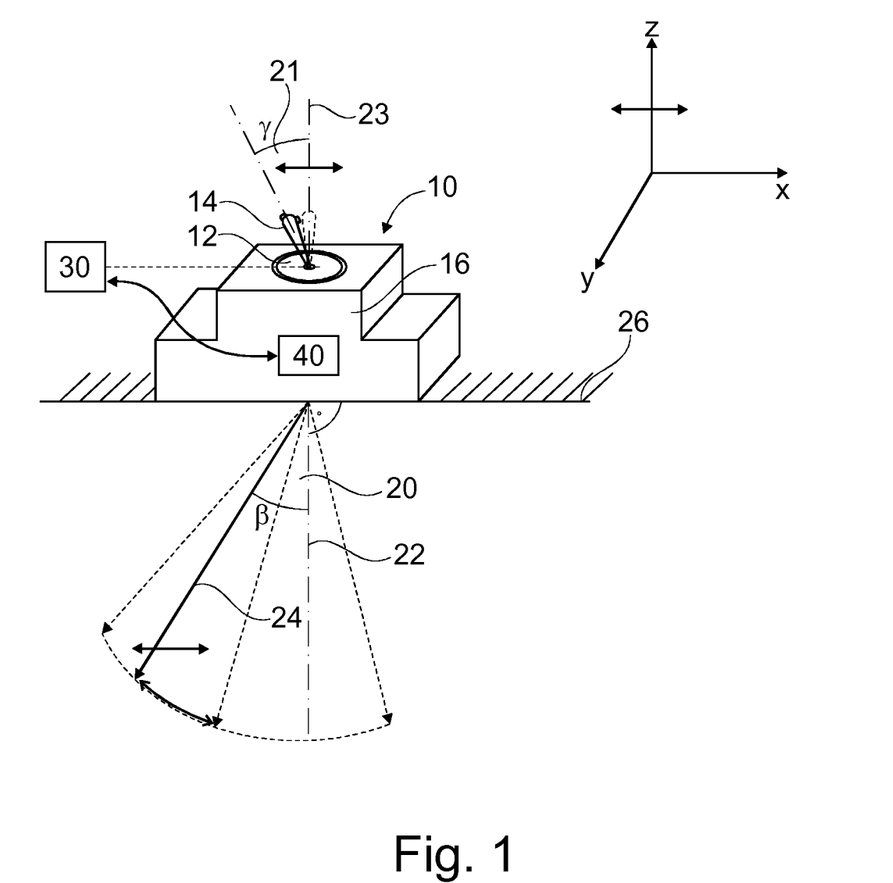
FIG. 1: a schematic representation of the ultrasonic test probe 10 of a device according to a first embodiment.
Figure 2:
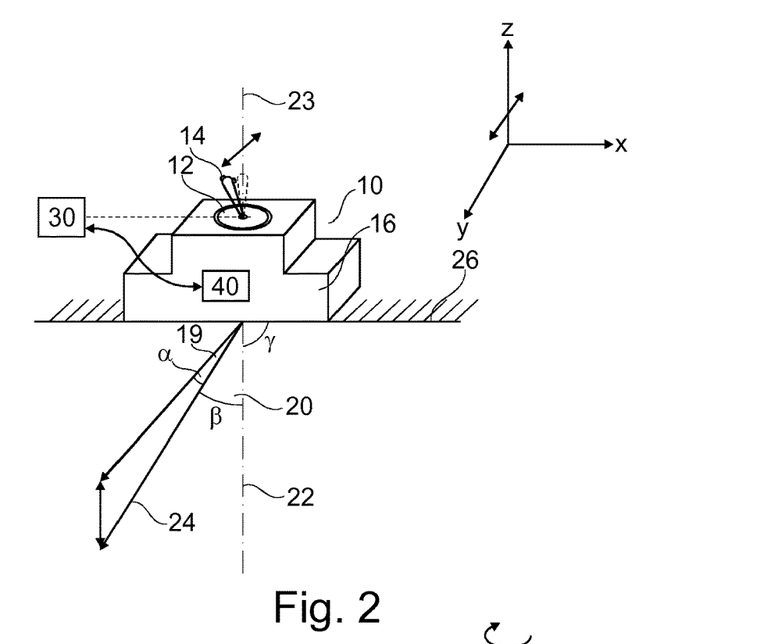
FIG. 2: a schematic representation of the ultrasonic test probe 10 of the device according to the first embodiment.
Figure 3:
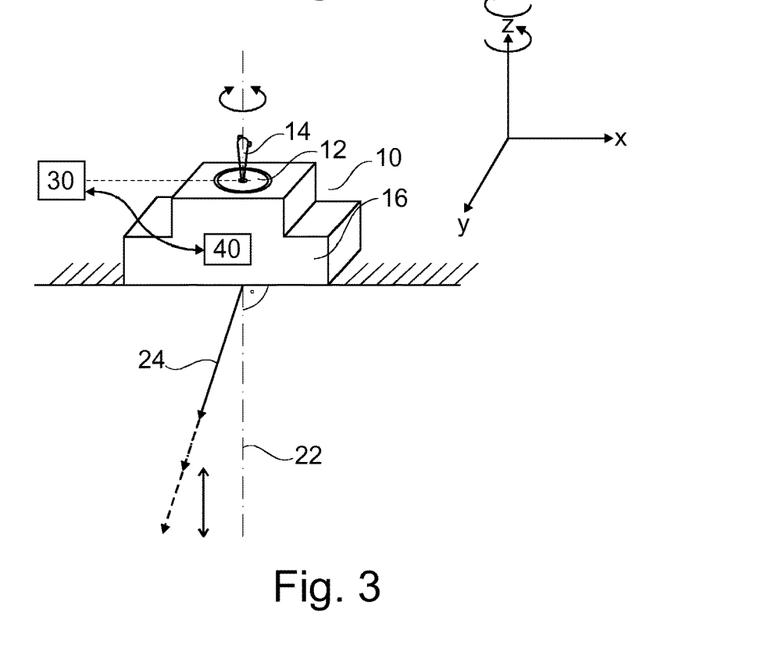
FIG. 3: a schematic representation of the ultrasonic test probe 10 of the device according to the first embodiment.

FIGS. 1 to 3 show schematic representations of an ultrasonic test probe 10 for use in a device, wherein the mode of operation of the input unit 12 according to a first embodiment, which is disposed on the ultrasonic test probe 10, is described.

The ultrasonic test probe 10 is disposed on the surface of a workpiece 26. It comprises a housing 16 and an input unit 12 disposed thereon and, not shown here, an ultrasonic transducer with several individually controllable segments for transmitting/receiving ultrasonic signals 24, which here are outlined as directional arrows. In the exemplary embodiment shown, the input unit 12 comprises a joystick with an operating lever 14 which has a defined rest position 23 and is pivotable in two planes that are perpendicular to each other, i.e. the x-z plane and the y-z plane, as is shown in FIGS. 1 and 2. The input unit 12 is configured for communication with an electronic control unit 30 comprising a transmitting/receiving unit 40 for communication with the ultrasonic transducer. The change of an input parameter of the joystick is converted via the transmitting/receiving unit 40 of the electronic control unit 30 into a change of an ultrasound parameter.

A deflection of the operating lever 14 relative to its rest position 23 in the x-z plane is detected as a change of a deflection angle 21 relative to the rest position 23 and processed by the input unit 12 as a control command by the user. The control command is transmitted to the transmitting/receiving unit 40 of the electronic control unit 30 and used for the control of the ultrasonic transducer. For example, a change of the deflection angle 21 leads to a change of the insonification angle 20 of the ultrasonic field in the workpiece.

In the exemplary embodiment shown, a change of the deflection angle 21 in the x-z plane is converted into a corresponding change of the insonification angle 20, which the emitted ultrasonic signals 24 form in the workpiece with the normal 22 on the workpiece surface 26, as shown in FIG. 1.

In contrast, the change of the deflection angle 21 of the operating lever 14 in the y-z plane causes a change of the transverse angle 19, with the insonification angle 20 remaining constant.

For example, an absolute change of the deflection angle 21 in the x-z plane of 25° is converted with a conversion factor of 1 into a pivoting of the insonification angle 20 by 25°.

In an embodiment, the conversion factor between the change of the deflection angle 21 of the operating lever 14 of the joystick and the change of the insonification angle 20 of the ultrasonic signals 24 in the workpiece can be varied, for example by means of the keys of the input unit 12 or the buttons on the GUI 50.

Moreover, the joystick is configured so as to be rotatable about its operating lever 14. A rotary movement of the operating lever 14 will be converted into a change of the focusing depth of the ultrasonic field in the workpiece. For example, the angle of rotation of the operating lever 14 of the joystick is detected and, depending on the direction of rotation, converted into an increase or reduction of the focusing depth, as is indicated by the partially dashed directional arrows of different lengths in FIG. 3. For example, the conversion factor between the angle of rotation and the change of the focusing depth can be varied, for example by means of the keys of the input unit 12 or the buttons on the GUI 50.

Figure 4:
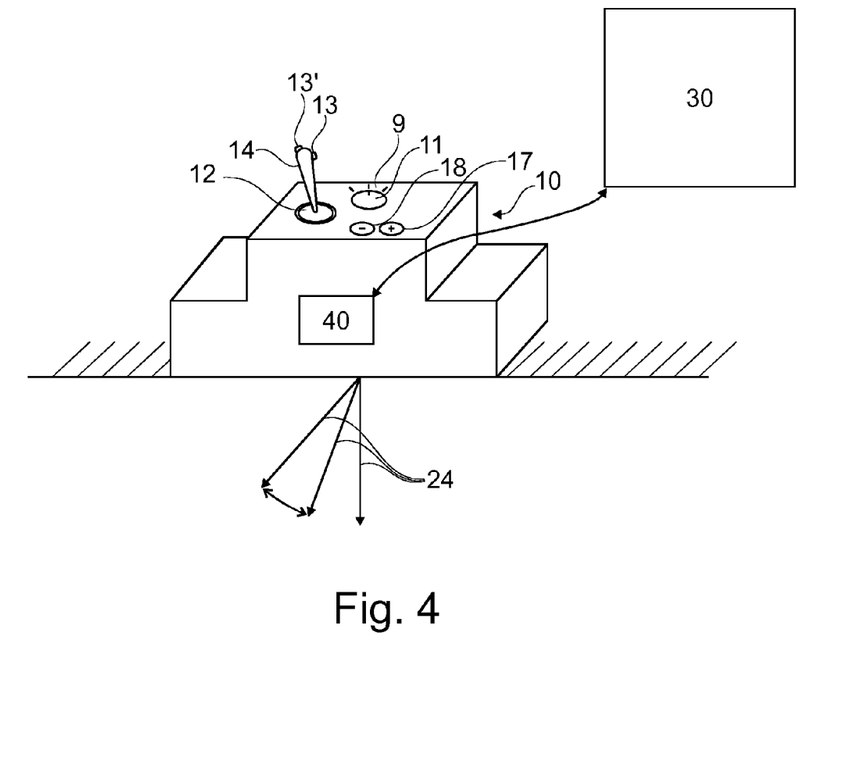
FIG. 4: an exemplary embodiment of an alternative ultrasonic test probe 10 for use in a device according to an embodiment.

FIG. 4 shows another exemplary embodiment of an ultrasonic test probe 10 of a device. Its input unit 12 comprises a plus key 17 and a minus key 18. The change of a conversion factor between the input parameter and the controlled ultrasound parameter is done by the user by actuating the plus key 17 or the minus key 18. An actuation of the plus key results in an increase of a conversion factor by a certain factor or a certain value, and an actuation of the minus key 18 leads to a corresponding reduction of the conversion factor.

All relevant conversion factors for the ultrasound parameters can be increased/reduced via the plus key 17 and the minus key 18. Which conversion factor is currently being changed is determined separately. For this purpose, the input unit 12 comprises a rotary disk 11 suitable for assuming various discrete positions 9. For example, the positions 9 are labeled with markings on the rotary disk 11 and the housing 16 of the ultrasonic test probe 10. The position 9 of the rotary disk 11 determines the ultrasound parameter whose conversion factor is varied via the plus/minus keys 17/18.

Moreover, the joystick comprises a key 13 disposed on the operating lever 14. An actuation of the key 13 by the user results in the freeze of the ultrasound parameters. It is preset, for example, that a change of the insonification angle 20 is carried out starting from an initial value of 0° in accordance with the change of the deflection angle 21 of the joystick. A deflection of the operating lever 14 in the x-z plane by 20° now causes a change of the insonification angle 20 from the initial value of 0° to the end value of 20°. By actuating the key 13, the end value of 20° is stored as the new initial value, and a new change of the deflection angle 21 in the x-z plane by 20° now causes a change of the insonification angle 20 from 20° to 40°.

Moreover, the joystick comprises another key 13' disposed on the operating lever 14. The key 13' is configured to trigger a snapshot of the received ultrasonic signals 24 upon actuation by a user.

Figure 5:
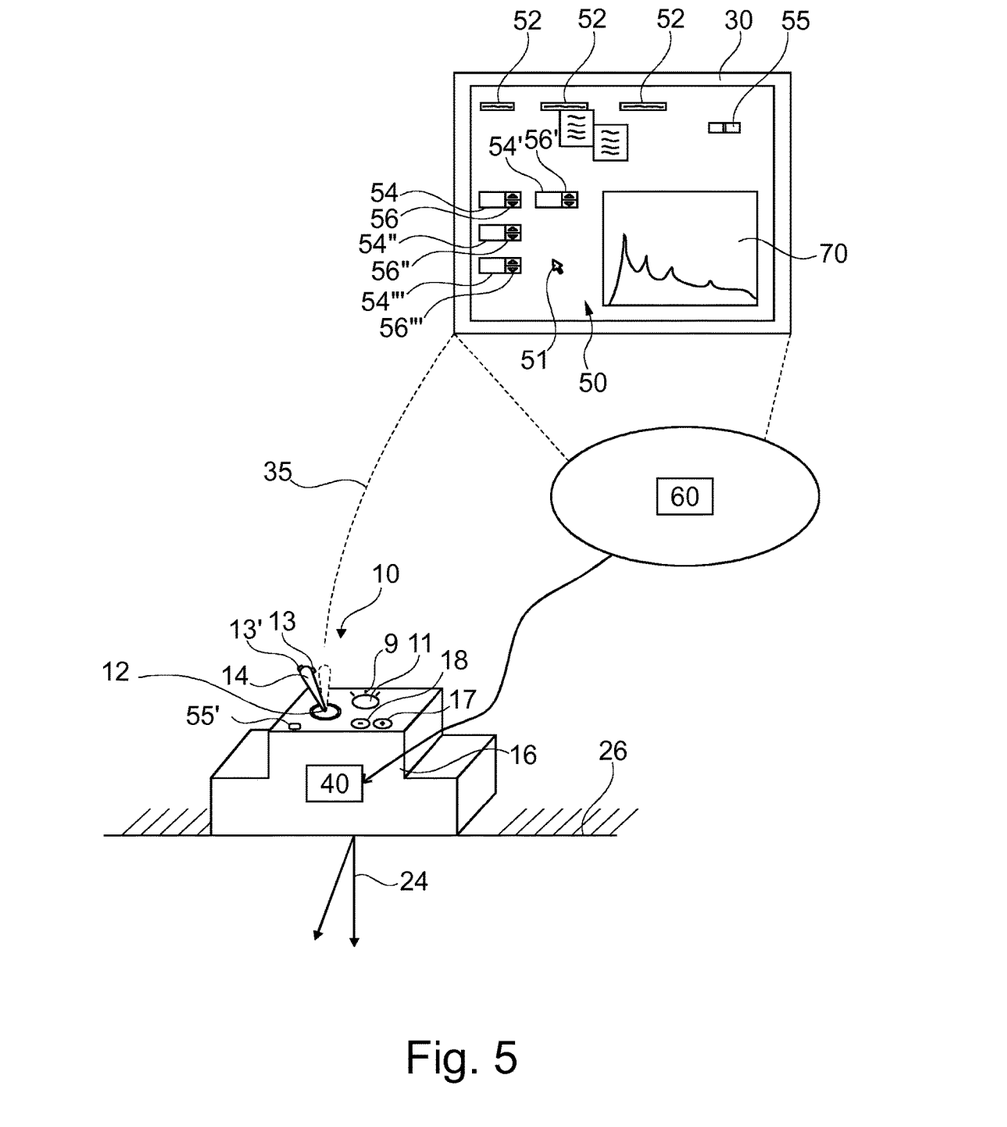
FIG. 5: a second exemplary embodiment of a device according to an embodiment with a graphical user interface.

FIG. 5 shows a schematic representation of another exemplary embodiment of a device for non-destructive ultrasound testing. The device comprises an ultrasonic test probe 10, which is configured for communication with an electronic control unit 30.

The ultrasonic test probe 10 is disposed on the surface of a workpiece 26, comprises a housing 16 and an input unit 12 disposed thereon and, not shown here, an ultrasonic transducer with several individually controllable segments for transmitting/receiving ultrasonic signals 24, which here are outlined as directional arrows.

By means of a WiFi connection 35, the input unit 12 is configured for communication with the electronic control unit 30. The electronic control unit 30 comprises a transmitting/receiving unit 40 configured for communication with the ultrasonic transducer for the purpose of transmitting or/and receiving ultrasonic signals 24, an evaluation unit 60 for processing received ultrasonic signals 24, and a graphical user interface 50 with a cursor 51.

Via the graphical user interface 50 of the electronic control unit 30, the ultrasound parameters of the emitted ultrasonic signals 24 can be varied by means of the transmitting/receiving unit 40. The ultrasonic signals 24 received by means of the transmitting/receiving unit 40 are displayed on the graphical user interface 50 by an imaging unit 70, for example as an A-scan, a B-scan or as a sector scan. The evaluation unit 60 of the electronic control unit 30, which is configured for communication with the transmitting/receiving unit 40, enables the processing of received ultrasonic signals 24, for example filtering them, amplifying them or storing them.

The processing of received ultrasonic signals 24 and the change of the ultrasound parameters of ultrasonic signals 24 emitted into the workpiece is effected by means of different buttons within the graphical user interface 50 that can be activated by the cursor 51.

The input unit 12 shown in FIG. 5 substantially corresponds to the input unit 12 known from FIG. 4. Reference is made to the explanations there. In addition, the input unit 12 shown in FIG. 5 comprises a switch 55', with which it is possible to switch between the two operation modes.

A movement of the operating lever 14 of the joystick in the x-z plane in the second operation mode is not converted into the change of the insonification angle 20, but into a corresponding movement of the cursor 51 within the graphical user interface 50. If the cursor 51 is located within the graphical user interface 50 on a button, the latter is activated by actuating the key 13.

FIG. 5 shows several buttons within the graphical user interface 50 in the form of pull-down menus 52, entry fields 54, 54', 54" and a virtual switch 55. For example, a starting parameter and an end parameter for changing an ultrasound parameter can be entered into the entry fields 54 and 54', and the number of steps in which the variation of the ultrasound parameter is to take place is entered into the entry field 54". For example, the insonification angle of the ultrasonic signals 24 is to be changed from 0° to 20°. The entry fields 54, 54', 54" have two arrow keys 56, 56', 56" that respectively increase or reduce a numerical value in the corresponding entry field 54, 54', 54" by a certain value. A value of 0 is entered into the entry field 54, and the value 20 is entered into the entry field 54'. The value 20 is also entered into the entry field 54". The start of a testing sequence, for example by means of a corresponding button within one of the pull-down menus 52, then causes a periodic pivoting of the angle of the insonification angle 20 from 0° to 20° in 20 steps of 1° each.

Via the pull-down menus 52, for example, it is possible to select for which ultrasound parameter the starting parameter and the end parameter as well as the number of steps for changing the corresponding ultrasound parameter takes place via the entry field 54, 54' and 54".

Other functions for processing the received ultrasonic signals 24 of for beam control are also located within the pull-down menu 52.

According to a particular exemplary embodiment, it is possible to switch at any time between the use of the joystick for manipulating the ultrasound parameter and the navigation by means of the graphical user interface 50, for example by means of a switch 55' on the input unit 12 and a corresponding virtual switch 55 within the graphical user interface 50.

In this exemplary embodiment, it is possible to follow on the graphical user interface 50 how the received ultrasonic signals 24 change when the ultrasound parameters are changed. For example, the change of the received ultrasonic signals 24 can be followed by means of the imaging unit 70.

For example, the change of an ultrasound parameter from a starting parameter towards an end parameter is displayed at the same time in the entry buttons 54 and 54'. Another entry button 54" is also provided in which the current conversion factor between the change of an input parameter and an ultrasound parameter is displayed.

With such a device, an intuitive presetting of the ultrasound parameters can be carried out by actuating a mechanical operating element of the input unit 12. It is possible to track what the settings are that are currently being used. A fine tuning of the parameters can be carried out via the buttons within the graphical user interface 50. For example, it may be beneficial to approximate an optimum focusing depth for the analysis of a flaw in the workpiece by rotating the operating lever 14 and to then set it precisely via the arrow keys 56' of an entry field 54'.

It is to be understood that even though numerous characteristics and advantages of various embodiments have been set forth in the foregoing description, together with details of the structure and functions of various embodiments, this disclosure is illustrative only, and changes may be made in detail, especially in matters of structure and arrangement of parts within the principles of the embodiments to the full extent indicated by the broad general meaning of the terms in which the appended claims are expressed. It will be appreciated by those skilled in the art that the teachings disclosed herein can be applied to other systems without departing from the scope and spirit of the application.

What is claimed is:
1. A device for the non-destructive ultrasound testing of workpieces, comprising:
an ultrasonic test probe with an ultrasonic transducer, the ultrasonic transducer including at least two individual segments configured to generate ultrasonic signals having predetermined ultrasound parameters into a workpiece and to receive ultrasonic signals from the workpiece;
an electronic control unit; and
an input unit, which is disposed on the ultrasonic test probe and includes an operating lever that is pivotable in at least one of a first plane and a second plane with respect to a defined rest position, the first plane being different from the second plane;
wherein the input unit is configured to detect a change in an input parameter of the operating lever including at least a deflection angle of the operating lever from the rest position in the first or second plane, to generate a control command based upon the detected input parameter change, and to transmit the control command to the electronic control unit; and wherein the electronic control unit is configured to convert a received control command to phase-accurately control the segments of the ultrasonic transducer based upon the detected input parameter change to effect change of an ultrasound parameter of the generated ultrasonic signals.

2. The device according to claim 1, wherein the input parameter comprises one or more of the following input parameters or/and their change over time: an actuating force applied to the operating lever, an angle of rotation of the operating lever from the rest position, and a contact position of the operating lever.

3. The device according to claim 1, wherein the input unit is configured for detecting control commands from a user by voice inputs or gesture control.

4. The device according to claim 1, wherein the electronic control unit is configured to convert a received control command into a change of an insonification angle of the generated ultrasonic signals based upon a detected change in the deflection angle of the operating lever in the first plane and to convert a received control command into a change of a transverse angle of the generated ultrasonic signals based upon a detected change of the deflection angle of the operating lever in the second plane.

5. The device according to claim 1, wherein the electronic control unit is configured for generating a snapshot of the received ultrasonic signals in response to a control command received from the input unit.

6. The device according to claim 1, wherein the electronic control unit is configured for carrying out a freeze, in response to a control command received from the input unit, of the current ultrasound parameters in response to actuation of a key disposed on the operating lever.

7. The device according to claim 1, wherein the electronic control unit further comprises a graphical user interface with a cursor and one or more activatable user interface objects, and the input unit further comprises a switch configured to reversibly change an operating mode of the input unit between a first operating mode and a second operating mode, wherein, in the first operating mode, the electronic control unit is configured to convert the received control command to phase-accurately control the segments of the ultrasonic transducer to change an ultrasound parameter of the generated ultrasonic signals, and wherein, in the second operating mode, the electronic control unit is configured to convert a received control commands to navigate the cursor over the graphical user interface.

8. The device of claim 7, wherein the electronic control unit is configured to convert the received control command based upon the detected input parameter change and a conversion factor between the input parameter and the controlled ultrasonic parameter.

9. The device of claim 8, wherein the input unit includes at least one actuatable key mounted to an input unit housing, wherein, in the first operating mode, the electronic control unit is configured to vary the conversion factor in response to actuation of the key, and wherein, in the second operating mode, the electronic control unit is configured to activate a user interface object selected by the cursor in response to actuation of the key.

10. The device of claim 9, wherein the input unit comprises a rotary disk configured to adopt one of a plurality of discrete positions, each discrete position corresponding to a different ultrasound parameter of the generated ultrasonic signals, and wherein, in the first operating mode, the input unit is configured to vary the conversion factor for the ultrasound parameter corresponding to the position adopted by the rotary disk in response to actuation of the key.

11. The device of claim 9, wherein at least one of the user interface objects is configured to generate a control command for changing an ultrasound parameter of the generated ultrasonic signals in the second operating mode when activated.

12. The device of claim 1, wherein the electronic control unit is configured to convert a received control command into a change of a focusing depth of the generated ultrasonic signals based upon a change of an angle of rotation of the operating lever from the rest position.

13. The device of claim 1, wherein the received control command effects a change in a single ultrasound parameter at a time based upon the detected input parameter change.

14. A method for non-destructive ultrasound testing of workpieces, comprising:
  generating, by an ultrasonic test probe including an ultrasonic transducer having at least two individual segments, ultrasonic signals with predetermined ultrasound parameters;
  detecting, by an input unit disposed on the ultrasonic probe, a change in an input parameter of an operating lever of the input unit from a defined rest position;
  generating, by the input unit, a control command based upon the detected input parameter change; and
  controlling, by the electronic control unit, the segments of the ultrasonic transducer in a phase-accurate manner based upon a received control command to effect a change in an ultrasound parameter of the generated ultrasonic signals;
  wherein, when the input parameter change comprises a change in a deflection angle of the operating lever from the defined rest position in a first plane, the electronic control unit controls the segments of the ultrasonic transducer to effect a change in an insonification angle of the generated ultrasonic signals; and
  wherein, when the input parameter change comprises a change in a deflection angle of the operating lever from the defined rest position in a second plane, the electronic control unit controls the segments of the ultrasonic transducer to effect a change in a transverse angle of the generated ultrasonic signal.

15. The method of claim 14, wherein the received control command effects a change in a single ultrasound parameter at a time based upon the detected input parameter change.

16. A method for non-destructive ultrasound testing of workpieces, comprising:
  generating, by an ultrasonic test probe including an ultrasonic transducer having at least two individual segments, ultrasonic signals with predetermined ultrasound parameters;
  detecting, by an input unit disposed on the ultrasonic probe, a change in an input parameter of an operating lever of the input unit from a defined rest position;
  generating, by the input unit, a control command based upon the detected input parameter change; and
  controlling, by the electronic control unit, the segments of the ultrasonic transducer in a phase- accurate manner based upon a received control command to effect a change in an ultrasound parameter of the generated ultrasonic signals;
  wherein the input parameter change comprises a change in an angle of rotation of the operating lever from the rest position, and the electronic control unit controls the segments of the ultrasonic transducer to effect a change in a focusing depth of the generated ultrasonic signals.

17. A method for non-destructive ultrasound testing of workpieces, comprising:
- generating, by an ultrasonic test probe including an ultrasonic transducer having at least two individual segments, ultrasonic signals with predetermined ultrasound parameters;
- detecting, by an input unit disposed on the ultrasonic probe, a change in an input parameter of an operating lever of the input unit from a defined rest position;
- generating, by the input unit, a control command based upon the detected input parameter change; and
- controlling, by the electronic control unit, the segments of the ultrasonic transducer in a phase- accurate manner based upon a received control command to effect a change in an ultrasound parameter of the generated ultrasonic signals;
- receiving, by the electronic control unit, a conversion factor between an input parameter and a predetermined ultrasound parameter of the generated ultrasonic signal; and
- controlling, by the electronic control unit, the segments of the ultrasonic transducer based upon the received control command and the received conversion factor to effect a change in the controlled ultrasound parameter.

18. The method of claim 17, comprising receiving, by the electronic control unit, a change of the conversion factor of the predetermined ultrasonic parameter in response to actuation of a key of the input unit.

19. The method of claim 18, comprising receiving, by the electronic control unit, a selection of the predetermined ultrasound parameter corresponding to a discrete position assumed by a rotary disk of the input unit.

* * * * *